United States Patent [19]
McIntyre

[11] Patent Number: 5,356,287
[45] Date of Patent: Oct. 18, 1994

[54] SIMULATING PRESENCE

[76] Inventor: Kevin M. McIntyre, 160 Commonwealth Ave., Ste. 801, Boston, Mass. 02116

[21] Appl. No.: 845,220

[22] Filed: Mar. 3, 1992

Related U.S. Application Data

[63] Continuation of Ser. No. 677,366, Mar. 26, 1991, abandoned, which is a continuation of Ser. No. 94,500, Sep. 9, 1987, abandoned, which is a continuation-in-part of Ser. No. 25,858, Mar. 16, 1987, abandoned.

[51] Int. Cl.$^5$ .................... G09B 5/04; G09B 19/00
[52] U.S. Cl. .................... 434/320; 434/236
[58] Field of Search ............. 434/157, 185, 236, 238, 434/319, 320, 321

[56] References Cited

U.S. PATENT DOCUMENTS

| | | |
|---|---|---|
| 3,271,883 | 9/1966 | Freeman . |
| 3,284,084 | 11/1966 | Cooper . |
| 3,358,390 | 12/1967 | Korn . |
| 3,416,242 | 12/1968 | Nisbet ............................ 434/321 |
| 3,641,507 | 2/1972 | Kosaka et al. . |
| 3,747,228 | 7/1973 | Yamamoto ....................... 434/320 |
| 3,920,903 | 11/1975 | Beller ............................. 434/320 |
| 3,934,226 | 1/1976 | Stone et al. .................... 340/172.5 |
| 4,139,954 | 2/1979 | Yamamoto ....................... 434/157 |
| 4,333,152 | 6/1982 | Best ............................. 364/521 |
| 5,033,969 | 7/1991 | Kamimura ........................ 434/322 |

FOREIGN PATENT DOCUMENTS 2121587 12/1983 United Kingdom ............... 434/185

*Primary Examiner*—Gene Mancene
*Assistant Examiner*—Cindy A. Cherichetti
*Attorney, Agent, or Firm*—Fish & Richardson

[57] ABSTRACT

A voice, familiar to a patient having a short-term memory loss problem, records comments, of the type that evoke responses, on a tape cassette followed by blank portions on the tape cassette to allow the patient to respond. The cassette is then played back for the patient over a personal cassette player through headphones to allow the patient to respond to the comments while the blank intervals are being played back.

14 Claims, 1 Drawing Sheet

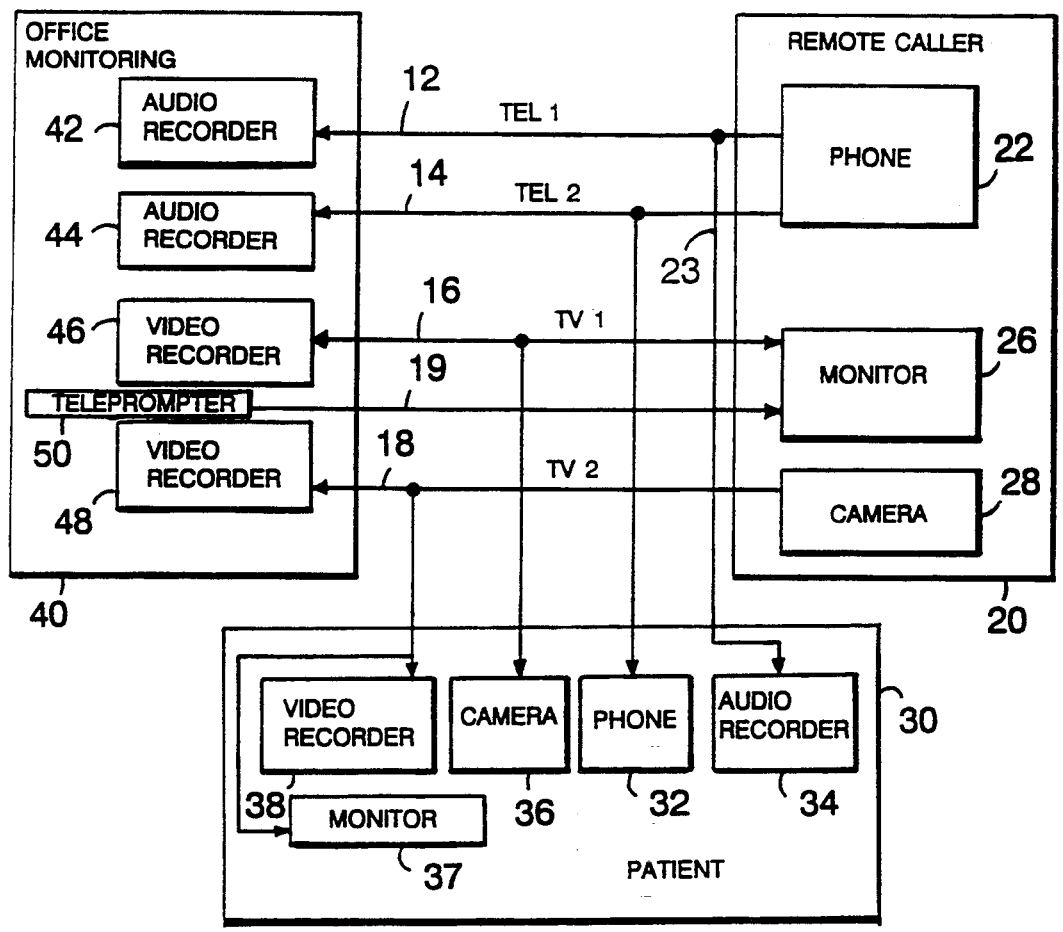
FIGURE

SIMULATING PRESENCE

This application is a continuing application of abandoned application Ser. No. 07/677,366 filed Mar. 26, 1991, of Kevin M. McIntyre for SIMULATING PRESENCE, which is a continuation of abandoned application Ser. No. 07/094,500 filed Sep. 9, 1987, which is a continuation-in-part of abandoned application Ser. No. 07/025,858 filed Mar. 16, 1987.

The present invention relates in general to treating memory loss and other mental, emotional and physical deprivation states and more particularly concerns novel techniques for treating patients with restricted short-term memory and reasonable long-term memory, such as Alzheimer patients, as well as patients with other mental, emotional and physical deprivations.

People with fading memories suffer a wide variety of emotional pains and intellectual torments. Their mental and emotional states are quite variable depending upon the stage of progression of the disease and the pathologic process responsible for the Alzheimer-like recent memory loss. They often suffer depression because their recent memory loss effectively cuts them off from anything and anyone except for their immediate environment. Thus, in unfamiliar surroundings such as a nursing home, they seek those individuals remembered, often through long-term memory which is very often preserved. These individuals are often mother, father and family, all of whom may be long-dead. The inability to find these individuals, to contact them, or even to have an explanation as to why they are not with the patient (if an explanation has been offered, it is, of course, not remembered), creates a sense of rejection and may result in severe depression. Loneliness can be a desperately painful problem since the recent memory loss prevents them from recalling explanations. Thus, the isolation created by recent memory loss can result in very serious degrees of depression, anxiety, fear, frustration, agitation and the whole range of negative human emotions.

A search of subclasses 236 and 319–22 of class 434 uncovered U.S. Pat. Nos. 2,892,040, 2,921,385, 3,176,927, 3,747,069, 3,747,228, 3,805,412, 4,372,554, United Kingdom Patent No. 1,400,279, U.S.S.R. Patent Nos. 827,029 and 1,005,153 and a publication entitled "A Voice-Operated Response Unit for Use in the Psychological Assessment of Motor Impaired Subjects."

It is an important object of this invention to provide improved techniques for treating patients with faded memories and other mental, emotional and physical deprivation states.

It has been discovered that a meaningful substitute for dense recent memory loss is the construction of an acceptable present environment for the sufferer. This environment is inhabited by familiar faces and voices and subjects. Critically constructed it can markedly reduce the painful emotional consequences of the loss of recent memory.

According to one aspect of the invention, a voice familiar to the patient is recorded with gaps between recorded comments to allow the patient to respond. In a specific embodiment of the invention, a child may record comments on a tape recorder followed by an unrecorded portion, then another comment and so on. The tape recording may then be played back to the parent over headphones.

In a more specific form of the invention referred to as "Idealized Visit Therapy" or "Recent Memory Reengagement Therapy," a recording is made of a patient visit during a visit by a significant other (S.O.), such as a child, other relative or friend, by audio or audiovisual means. Selected materials are brought up for discussion by the S.O. based on the S.O.'s knowledge of patient's interests, friends, family or other matter, i.e., significant aspects of patient's life which deal with positive emotion, concern, interest, humor. The recording of the visit is then reviewed by a monitor/evaluator with the S.O. or family. If the visit appears to have been a positive experience, the patient's voice and visual participation is then removed from the recording. Likewise, any emotionally negative aspects of the visit are erased (i.e., "Idealized Visit Therapy"). The recording may then be played back to the patient, to produce a simulated visit, who may be expected to fill the spaces in the taped visit with nearly the same responses, both verbally and emotionally, as experienced at the original visit.

Thus, this aspect of the invention features the recording of conversation between the patient and an S.O. to be followed by the editing of that recording for the sections most beneficial to the patient, elimination of the patient's part in the recording and replaying for the patient. The patient will benefit to the extent that the patient believes that it is an actual visit by someone the patient cares about; to the extent by which it reduces anxiety either by focusing the patient's attention on someone the patient cares about, or by distracting the patient from other troubling thoughts; to the extent to which the patient is entertained and pleased, even if the patient realizes it is a recording; by virtue of the fact that the patient with a recent memory deficit will not recall the tape or the content and will see it as a first, fresh experience each time it is played; to the extent that aspects of recent memory remain competent, the reinforcement of the support provided by the simulated visit may be expected to reduce anxiety, and elevate mood; to the extent that certain commands which facilitate the patient's well being can be incorporated on the tape (for example, "exercise your arms," "brush your teeth," "go to nurse Jones") and the patient can follow these commands; and because of the reduction in mood-affecting medication necessary for treatment of the disease-state.

Benefit for the care-provider includes reduction in need for personal attention, drug therapy, group therapy; facilitation of patient care requirements as noted above (exercise, personal hygiene, etc.); and in an enhanced sense of effective care-giving.

In a second aspect of the invention, the S.O. may be people who are less related or less well-known to the patient, or a synthesizer. Tapes are made which have discussions of subjects particularly interesting to the patient. The patient is able to choose these subjects directly (by asking for them), or indirectly by showing boredom in response to another tape, repetition of key words or specifically requesting such a tape in response to a question. In preferred embodiments, the patient may prepare the tapes to be used for his or her treatment, prior to onset of the disease affecting the patient.

More specifically, this aspect of the invention features a method of treating a patient with restricted short-term memory which method includes the steps of, creating a series of comments (e.g., questions or anecdotes) on a memory signal storage means (e.g., a tape, or a synthesizer), playing a first of these comments to the patient, and playing a second of the comments to the patient. In this method, the second comment is chosen dependent upon the reaction of the patient to the first comment.

In preferred embodiments, the reaction is the use of a key word (e.g., mother, yes or no) by the patient, an extended silence of the patient, anger or frustration expressed by the patient, or by specific request of the patient.

In a third aspect, the invention features a generic voice set. This set consists of a plurality of memory signal storage fragments, each fragment comprising a signal, wherein the signal can be converted by a signal converter to an audible sound perceptible to a human. The sound is recognizable by the human as a comment, and the comment is the same in each fragment, except that the sound in each fragment differs in its character. The set is suitable for determining a sound which is beneficial to a human having restricted short-term memory. Thus, this aspect provides a set of tapes, or similar means, having a series of comments, made either as recordings or by synthetic processes, which are generic. These tapes include a series of comments, questions or other suitable phrases which are designed to discover subject matters to which a patient responds most favorably. These generic tapes also contain the same comments made by a set of various voices (including synthetic such voices), using different intonations, so that the sound most beneficial to the patient can be discovered.

In preferred embodiments, a single generic sampler tape is provided. This tape has a series of short comments each made by one of a variety of different voices. Using this tape the best-suited voice is chosen for a patient (this is the Voice to which the patient most favorably responds). A second tape is then used to discover the best-suited subject matter for a patient. This tape is chosen from a library of tapes having identical subject matter, but each made by a variety of different voices—the tape corresponding to the best-suited voice discussed above is chosen. By playing this tape, the subject matter to which the patient reacts most favorably can be discovered. Finally, a third tape is chosen from a library of such tapes, this tape is made from the most-favored voice and on the most-favored subject matter.

Thus, this invention provides means to custom-make a tape library for a particular person. This library is chosen from a master library having a wide variety of recordings on different subject matter, made by a variety of voices. This enables a patient having no available S.O. to be cared for, using specific generic tapes.

Numerous other features, objects and advantages of the invention will become apparent from the following specification when read in connection with the accompanying drawing, the single figure of which is a block diagram illustrating the logical arrangement of a system according to the invention.

A tape recorder, which may be a conventional easily transportable cassette recorder. A person, with a voice familiar to the patient, such as the patient's child, broadcasts into a microphone, with comments or questions of a type that would normally evoke a response, to record these comments on magnetic tape in the tape recorder. Each comment is followed by a silent unrecorded interval on the tape sufficiently long to allow a person to respond to the comment. The cassette is then rewound and turned to the playback mode that the patient may hear the recorded comments through headphones or see and hear the person with the familiar voice via an audiovisual means. Although not essential to the invention, headphones are advantageous since they block out extraneous noise, and can cause the user to think that he/she is involved in a telephone conversation.

It is not necessary that the tape recorder on which the recording is made be the same one used by the patient to play back the recorded information. It may be advantageous to have a personal playback cassette player only available for the patient to play back the tape recording. The person may extemporaneously make the comments, or, if preferred, read the comments from a script, leaving a blank interval on the tape between each comment. As an example of a suitable recording, person might say, "Hello Mother, this is Kevin. How are you?" (Blank). "It is good to see you looking so well. Did you enjoy your day?" (Blank). "What television show would you like to watch?" (Blank). The tape may then be played back to the patient, over headphones, allowing patient to respond to each comment. In an actual embodiment of the invention, the results were astonishing. The patient's eyes brightened, and she responded to the questions. The invention converted a lethargic, lack-of-interest disposition into a more animated, interested disposition. And the manifestations of depression, sadness, loneliness and boredom evident before the intervention were supplanted by an obvious joy and pleasure at onset of the "simulated visit."

According to another form of the invention, conveniently referred to as "Idealized Visit Therapy" or "Recent Memory Re-engagement Therapy," a recording is made of a patient visit during a visit by an S.O., such as a child, other relative or friend, by audio tape recorder, video tape recorder, sound movie camera, or other suitable means. The S.O. introduces selected materials for discussion by S.O. based on S.O.'s knowledge of patient's interests, friends, family or other matters; that is, significant aspects of the patient's life which deal with positive emotion, concern, interest or humor. The recording of the visit is then reviewed by a monitor/evaluator with the S.O. or family of the patient. If the visit thus recorded appears to have been a positive experience, the patient's voice and visual participation (if an audiovisual recording) is then removed from the recording along with any emotionally negative aspects of the visit. The recording thus modified is then played for the patient, who may be expected to respond in a manner similar to his response during the original visit. Thus, the patient receives the same or better uplift, experienced by the patient during the live visit. Furthermore, the impact is superior to pharmacological interventions, such as tranquilizers, sedatives and other psychotropic agents.

The invention takes advantage of the limited short-range memory of the patient. The same tape may be played repeatedly and have the same beneficial effect on the patient upon each playing. The invention may be used in connection with an audio tape or a video tape. In the case of the video tape, the image of the familiar person could be reproduced for the patient. It is also within the principles of the invention to record the familiar voice digitally in a read-only memory, or a programmable read-only memory and use digital data processing techniques to leave the gaps for responses.

In order to broaden the reservoir of subject matter and individuals for the patient's benefit, with the purpose of more completely supplementing the individual's fading memory and also more fully developing an environment acceptable and desirable to the patient, a bank of subjects and individuals in addition to the S.O. is developed. In addition, a simulator is used to create voices of varying pitch or wavelength which are chosen to suit the particular patient and the need of the patient. The simulator is better able to compete with any noise the patient is making, and capture the patient's attention, since the wavelength of sound is chosen to correspond to that of the patient's own sounds. Further, the simulator is programmed to be able to change its "conversation" dependent upon key words from the patient.

The subjects to be played are selected directly by the patient, by a companion or attendant, by a spoken "key" word or subject, or by the silence which is created when the patient no longer interacts with an on-going simulated presence, thus signaling, perhaps, boredom or disinterest. An example of such an interactive conversation follows.

EXAMPLE 1: "KEY"WORD—"MOTHER"

Simulator's voice (S.V.): "Hello, Mother! How are you today! This is Jack, your son."

Patient Response (P.R.): "I'm fine. How are you, Jack? Of course I know who you are!"

S.V.: "You're looking very well, mother. Your hair looks great! It looks like you just had a permanent!"

P.R.: "Really? Oh, yes! My mother did it for me. Just this morning."

S.V.: "And how is your mother doing?"

P.R.: "I'm not sure, okay, I guess."

S.V.: "I bet you miss your mother when she's not here."

P.R.: "Of course I miss my mother! Who wouldn't." (Annoyed).

In this conversation "mother" has been mentioned 6 times, 4 times in the P.R. and 2 times in the S.V. At this point, a different S.V. is initiated based on the fact that a key word was used 6 times, or that the key word was used twice in the P.R.; or by selection by an attendant who asks "Would you like to talk with your mother?" (if mother is indeed alive and able to make an S.V., which is unlikely) or "Would you like to talk about your mother for a while?" Alternatively, the patient may select "mother" from the panel of subjects and designated individuals which make up her array of potential S.V.s.

A tape having a discussion of the patient's mother then starts. The tape can be made by a healthy sibling of the patient, who knew their mother well and knew the relationship and commonalties between the patient and patient's mother. An example of such a tape follows.

EXAMPLE 2: SIBLING

S.V.: (Sibling) "Helen, this is your sister Mary. Remember when we used to walk down the beach at City Point with mother? Remember how Ma's hair, that long black hair that never turned grey, would blow in the wind?"

P.R.: "Yes. I remember."

S.V.: "And she was always humming a song and sometimes we'd sing together."

S.V.: Begins slowly to sing the song, coaches the patient to sing along. After the song the "conversation" continues about mother.

S.V.: "Do you remember when we visited Ireland with mother on her 75th birthday?"

P.R.: "Of course I remember! What do you think I am?" (Losing patience and perhaps attention span).

S.V.: "I remember when we went out to Athlone and went boating on the River Shannon, all the way up through Loch Ree. It was so beautiful looking from the boat to the Irish Country side. Would you like to look at some of the pictures we took in Ireland?"

If the patient answers: "No! I don't care about pictures! And I don't care about Ireland!" then the "conversation" continues with S.V., keyed on the term "No."

If the patient answers: "Oh, yes! That would be lovely!" A voice-activated movie or slide set, of Ireland is produced.

If the patient does not answer, the tape continues.

A similar selection of voice-key, or "silence"-key, can be used to attempt to follow-up and reinforce the patient's apparently desirable associations and memories— and also to discontinue S.V.s in which the patient has lost interest.

The repertoire of tapes for the patient is broadened further by developing a "Simulated Presence" in the absence of the significant other. For example, a series of questions and a series of brief comments and anecdotes is developed by the patient's S.O. in the absence of the patient. This consists of a bank of questions, comments and observations by the S.O. each of which is evaluated for impact on the patient. These questions, comments, and anecdotes, are then played for the patient with close attention to the patient's response so that sufficient time can be left for the patient to complete his response. This can be accomplished manually, by the person supervising the simulated conversation, or by a voice-controlled automatic mechanism. The patient's response is then graded for emotional and intellectual content and responsiveness using parameters such as: appropriateness, pleased versus displeased response, relief versus agitation. Selection of the most desirable "pieces" from the bank is made and a tape, audio or audio-visual, developed. This tape is evaluated for its "interactive" quality using a series of emotional and intellectual indices. Editing of the tapes to perfect its content continues until the desired result is obtained.

In the process of developing the "bank" of questions, and comments, by the S.O., a systematic review with the patient is carried out and recorded. Every family member, friend, hobby, activity, sport, location, and pet thought to be important to the patient will be mentioned by the S.O. or another interviewer so that a bank of the patient's most cherished experiences and associations is developed. From this exploration of the patient's memory, a further series of comments, and questions, is developed and evaluated in terms of the patient's response.

A subsequent step is to identify a limited number of key terms, names of friends or family which seem to give most pleasure or satisfaction when discussed. A special series of comments and questions are developed and taped by the S.O. until a satisfactory content is developed under each of these key terms.

When a patient has no known close relative it is possible to use "simulated presence" interactive audio and audio-visual programs in a form which are used generically, the emphasis being on the sound, character and content of the speaker's voice. The purpose of a generic tape series is to provide an alternative to, or reduction in dose of, drug therapy in those individuals for whom the therapy is effective.

EXAMPLE 3: GENERIC TAPE

Simulating (Generic) Visitor: "Hello, Sir! How are you today?" (Space for response) "May I visit with you for a while?"

If patient answers "Yes," this tape is continued; if patient answers "No," an alternative tape dealing with another subject, such as music, baseball, or fishing is used. Simulating (Generic) Visitor continues, after some additional small talk: "I understand you are very interested in baseball?" If patient answers "Yes", the baseball "visitor" tape is used as follows.

"Ted Williams, the "splendid splinter" was the greatest hitter who ever tapped his bat on home-plate, at least as far as I am concerned. What do you think, my friend?" If the patient answers "Yes", the "Ted Williams" Visit tape is continued. If the patient answers "Joe DiMaggio", the "Joe Dimaggio" tape, which is in the bank, will be played. If the patient answers "No" the tape may be changed or a "bridging" tape may be used to find a word or subject "key" which might identify the patient's preference, e.g., music, sports, or theatre.

The generic tapes have a series of different voices, styles, intonations and characters—all with the same script. Examples range from mild, soft spoken and gentle, through confident and firm to occasionally aggressive voices. Tapes utilize both males and females, young and old, in order to allow identification of some of the most appealing and effective voices for a particular patient. These varying voice personalities will engage in a series of "generic" conversations, questions, comments, stories, including a number of areas of general interest: weather, sports, history, current events, family, or business. The patient's responses to these generic therapies are evaluated as to efficacy, impact on medication requirement, and other suitable criteria.

Responses may be measured in two ways. The first is a recognized objective measurement, using psychological instruments to measure the impact of the tapes on emotion, affect, and cognitive function. Further, the requirement for psychoactive drugs may be reduced, or the need eliminated, with these tapes. Such changes are readily measured and are an accurate and useful measure of a patient's response. A second measurement entails the development of an index including affective indices, such as eye appearance, eye contact, psychological posture, attentiveness to the tape, engagement in conversation, and verbalization. Such measurement will be made by comparison with a baseline period during which the patient is not treated. A series of baselines covering a variety of moods would be desirable. Accordingly, comparison of the impact of a tape on the patient when the patient is in other moods could be made.

The use of each type of tape, whether generic, sibling or S.O., will depend upon each patient and the availability of S.O.'s. If a patient is extremely demented then generic tapes are a better starting point for treatment; if the patient is intellectually relatively intact then non-generic tapes are better. However, each tape must be evaluated for its content, the quality of patient response, the amount of conceptual engagement, and the passiveness or activeness of the response. After such evaluation the patient may operate the tapes alone. A tape may also be left with the patient without supervision once the patient response can be predicted with reasonable certainty. Prior to this the tape must be used only with proper supervision to ensure that it does not induce too much agitation.

One particularly useful type of tape is that which is made by the patient himself or herself. Some types of diseases that are treated by these tapes are inherited, Thus, a person may recognize that he is a potential patient. With guidance this person can construct tapes which are particularly relevant to him. Early use of these tapes will help to delay onset of disease, and will help delay the time at which drugs are necessary for treatment. Since the person knows himself intellectually better than any other person, such tapes can be individually designed to best benefit that patient. Further, these tapes will be useful for the patient's children, or spouse, or close relatives, should they develop the disease either before or after his death.

With reference to the drawing, there is shown a block diagram illustrating the logical arrangement of a system according to the invention for recording therapeutic recordings. A caller at caller location 20 may call a patient at patient location 30, and the call may be monitored at monitoring office 40. The caller may use caller transmitting station 22 to converse with the patient at patient transmitting station 32. The two-way conversation between caller and patient may occur over line 14 and recorded by recorder 44 at monitoring office 40. Recorder 44 may record both sides of the conversation. Another line 12 may connect the caller to recorder 42 at monitoring office 40. Line 23 may record only the caller's side of the conversation. The caller's conversation only may also be recorded by recorder 34 at patient location 30. It is not necessary that there to be two distinct lines to obtain a recording of the caller's conversation only. For example, the conversation on line 14 could be recorded and edited. Alternatively, the caller's side could be recorded by a recorder at caller location 30.

The system may also provide video recordings. Video camera 36 may image the patient and provide a video signal on line 16 allowing the caller to view the patient image on monitor 26 and be recorded by video recorder 46 at monitoring office 40. Video camera 28 may view the caller to provide a video signal on line 18 by video recorder 48 at monitoring office 40, and may also be recorded by video recorder 38 at patient location 30. The patient may view the image of the caller on monitor 37. The videotape recording may be used for additional evaluation and editing to improve therapeutic effect as described above. In addition, the videotape may be preserved for future reference or for the family member caller.

According to another feature of the invention, teleprompter 50 may broadcast on line 19 a video signal to caller monitor 26 displayed as a text furnishing guidance to the caller in partially or completely structuring the conversation with the patient.

Locations 20, 30 and 40 may be wherever convenient. For example, the caller may be calling from a location near the patient, or in monitoring office 40. It may be in a booth or portable unit at patient location 30. Communication could be with an intercom or other suitable device.

It is evident that those skilled in the art may now make numerous uses and modifications of and departures from the specific embodiments described herein without departing from the inventive concepts. Consequently, the invention is to be construed as embracing each and every novel feature and novel combination of features present in or possessed by the apparatus and techniques herein disclosed and limited solely by the spirit and scope of the appended claims.

Other embodiments are within the claims.

What is claimed is:

1. A method of treating a patient with restricted short-term memory which method includes the steps of,
    recording a sequence of comments voiced by a voice familiar to said patient,
    and playing back the recorded comments to said patient while leaving blank recorded intervals between said recorded comments for said patient to respond to said recorded comments,
    wherein said voice is the voice of a parent, child or spouse of said patient.

2. A method of treating a patient with restricted short-term memory which method includes the steps of,
    recording a sequence of comments voiced by a voice familiar to said patient,
    and playing back the recorded comments to said patient while leaving blank recorded intervals between said recorded comments for said patient to respond to said recorded comments,
    wherein said step of recording a sequence of comments voiced by a voice familiar to said patient includes recording a sequence of comments voiced by a voice familiar to said patient and by said patient during an actual visit by the person having the voice familiar to said patient with said patient evoking an uplifting response by said patient to said visit, and further including,
    deleting the comments voiced by said patient during said visit to form said intervals between said comments voiced by said voice familiar to said patient for said patient to respond to the latter comments.

3. A method of treating patients in accordance with claim 2 wherein said visit may include events evoking an unpleasant response from said patient, and further including
    the step of deleting portions of said recording that record said events that evoked an unpleasant response from said patient.

4. A method of treating patients with restricted short-term memory which method includes the steps of,
    recording a sequence of comments voiced by a voice familiar to said patient,
    and playing back the recorded comments to said patient while leaving blank recorded intervals between said recorded comments for said patient to respond to said recorded comments,
    wherein said step of recording comments includes recording each comment on magnetic tape and leaving a blank interval on said magnetic tape between comments,
    and playing back said magnetic tape including the blank portions to allow the patient to respond while said blank portions are being played back and further including,
    the steps of recording the picture of the person voicing said comments on said magnetic tape.

5. A method of treating a patient suffering from an illness characterized by restricted short-term memory and reasonable long-term memory, wherein said restricted short-term memory causes said patient to suffer at least one of emotional pains and intellectual torments which method includes the steps of,
    recording a sequence of stimulus signals characteristic of at least one of faces, voices and subjects recallable by said patient from said patient's reasonable long-term memory but not recallable by said patient from said patient's restricted short-term memory,
    and playing back said sequence of stimulus signals while leaving blank recorded intervals between consecutive ones of stimulus signals of sufficient duration to allow said patient to respond to the recorded stimulus signals to construct an acceptable present environment for the patient that relieves at least one of emotional pains and intellectual torments of said patient caused by said restricted short-term memory.

6. A method of treating a patient suffering from an illness characterized by restricted short-term memory and reasonable long-term memory causing said patient to suffer at least one of emotional pains and intellectual torments which method includes the steps of,
    recording a sequence of stimulus signals characteristic of at least one of faces, voices and subjects recallable by said patient from said patient's reasonable long-term memory but not recallable by said patient from said patient's restricted short-term memory,
    and playing back said sequence of stimulus signals while leaving blank recorded intervals between consecutive ones of stimulus signals of sufficient duration to allow said patient to respond to the recorded stimulus signals to construct an acceptable present environment for the patient that relieves at least one of emotional pains and intellectual torments of said patient caused by said restricted short-term memory,
    wherein said at least one of familiar faces, familiar voices and familiar subjects is from the group consisting of a parent, child, spouse and friend of said patient.

7. A method of treating a patient suffering from an illness characterized by restricted short-term memory and reasonable long-term memory causing said patient to suffer at least one of emotional pains and intellectual torments which method includes the steps of,
    recording a sequence of stimulus signals characteristic of at least one of faces, voices and subjects recallable by said patient from said patient's reasonable long-term memory but not recallable by said patient from said patient's restricted short-term memory,
    and playing back said sequence of stimulus signals while leaving blank recorded intervals between consecutive ones of stimulus signals of sufficient duration to allow said patient to respond to the recorded stimulus signals to construct an acceptable present environment for the patient that relieves at least one of emotional pains and intellectual torments of said patient caused by said restricted short-term memory,
    wherein said step of recording stimulus signals includes recording a sequence of comments voiced by a voice familiar to said patient and by said patient during an actual visit by the person having the voice familiar to said patient with said patient evoking an uplifting response by said patient to said visit and further including,
    deleting the comments voiced by said, patient during said visit to form said blank recorded intervals.

8. A method of treating a patient suffering from an illness characterized by restricted short-term memory and reasonable long-term memory, wherein said restricted short-term memory causes said patient to suffer at least one of emotional pains and intellectual torments wherein said recording step includes the steps of, recording a sequence of comments voiced by a voice familiar to said patient, and playing back the recorded comments to said patient while leaving blank recorded intervals between said recorded comments for said patient to respond to said recorded comments, wherein said step of recording comments includes recording each comment on magnetic tape and leaving a blank interval on said magnetic tape between comments, and playing back said magnetic tape including blank portions to allow the patient to respond while said blank portions are being played back.

9. A method of treating a patient suffering from an illness characterized by restricted short-term memory and reasonable long-term memory causing said patient to suffer at least one of emotional pains and intellectual torments wherein said recording step includes the steps of, recording a sequence of comments voiced by a voice familiar to said patient, and playing back the recorded comments to said patient while leaving blank recorded intervals between said recorded comments for said patient to respond to said recorded comments, wherein said step of recording comments includes recording each comment on magnetic tape and leaving a blank interval on said magnetic tape between comments, and playing back said magnetic tape including blank portions to allow the patient to respond while said blank portions are being played back, and recording the picture of the person voicing said comments on said magnetic tape.

10. A method for treating a patient with restricted short-term memory including the steps of, recording at least portions of a live conversation between a caller talking and said patient talking in spaced locations, making a playback recording that is a recording only of the caller's portions of said live conversation and unrecorded portions corresponding to when said patient was talking, and playing at least a portion of said playback recording with said caller's portions to said patient.

11. The method of claim 10 and further including, editing said caller's portions in said playback recording to enhance therapeutic value for the treatment of said patient to provide an edited recording, and playing back the edited recording to said patient.

12. The method of claim 10 and further including, the step of furnishing textual material to said caller to assist said caller in conversing with said patient.

13. A method for treating a patient with restricted short-term memory including the steps of, recording a live conversation between a caller talking and said patient talking in spaced locations, making a playback recording that is a recording only of the caller's portions of said live conversation and unrecorded portions corresponding to when said patient was talking, and playing at least a portion of said playback recording with said caller's portions to said patient, and making a video recording of the image of said patient during said live conversation.

14. The method of claim 13 further including, displaying an image of said patient during said live conversation.

* * * * *